United States Patent
Xu et al.

(10) Patent No.: US 10,167,456 B2
(45) Date of Patent: Jan. 1, 2019

(54) BIFUNCTIONAL LIPASE MUTANT AND METHODS OF USING SAME

(71) Applicant: Jiangnan University, Wuxi (CN)

(72) Inventors: Yan Xu, Wuxi (CN); Xiaowei Yu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 1 day.

(21) Appl. No.: 15/876,159

(22) Filed: Jan. 21, 2018

(65) Prior Publication Data
US 2018/0148700 A1 May 31, 2018

Related U.S. Application Data

(63) Continuation of application No. 15/038,364, filed as application No. PCT/CN2014/072549 on Feb. 26, 2014, now Pat. No. 9,890,367.

(51) Int. Cl.
| | |
|---|---|
| *C12N 11/00* | (2006.01) |
| *C12N 9/20* | (2006.01) |
| *A21D 8/04* | (2006.01) |
| *A23L 29/00* | (2016.01) |
| *A23L 7/109* | (2016.01) |
| *C12N 15/81* | (2006.01) |

(52) U.S. Cl.
CPC ............ *C12N 9/20* (2013.01); *A21D 8/042* (2013.01); *A23L 7/109* (2016.08); *A23L 29/06* (2016.08); *C12N 15/815* (2013.01); *C12Y 301/01003* (2013.01); *A23V 2002/00* (2013.01)

(58) Field of Classification Search
None
See application file for complete search history.

(56) References Cited

U.S. PATENT DOCUMENTS 9,890,367 B2 * 2/2018 Xu .......................... C12N 9/20

* cited by examiner

*Primary Examiner* — Hope Robinson
(74) *Attorney, Agent, or Firm* — Na Xu; IPro, PLLC

(57) ABSTRACT

The present invention provides a novel dual-function lipase mutant and its application in processing of flour products. The amino acid sequence of the lipase has one of the following amino acid substitutions: P298T, P298T/H317P, P298T/H317P/V326S, P298T/T218S/S234F, P298T/H317P/P168L/A129S, P298T/S234F/K161R/V326S, wherein the substitutions are relative to a parent amino acid sequence set forth in SEQ ID NO:1; wherein the lipase mutant maintains a triglyceride and lecithin hydrolysis activity and good performance in thermostability. The mutants have good performance in processing of flour products, while they can significantly whiten the bread or other products in processing of flour products and significantly increase the specific volume in bread baking process.

2 Claims, No Drawings
Specification includes a Sequence Listing.

BIFUNCTIONAL LIPASE MUTANT AND METHODS OF USING SAME

FIELD OF THE INVENTION

The present invention relates to a novel dual-function lipase variant and its application in processing of flour product. Specially, the lipase variant with enhanced characteristics may be obtained by molecular biology techniques, which is suitable for processing of flour products. The present invention relates to the field of enzyme engineering.

BACKGROUND

Enzyme plays an irreplaceable role in improvement of baking and flour quality because of its unique biological characteristics. Currently, the usage of enzymes in processing of flour products has become a mainstream trend.

The flour used for bread baking contains glycerol phospholipids and triglycerides. When the glycerol phospholipids were partially hydrolyzed into hemolysis glycerophospholipids and triglycerides were partially hydrolyzed into monoglycerides or diglycerides, the hemolysis glycerophospholipids, monoglycerides and/or diglycerides would work as surfactants during emulsion reaction. In addition, emulsification plays a part in strengthening the dough gluten, enhancing urgent expansion in the furnace and expanding volume, which makes the bread uniform, soft and have a better taste. Therefore, addition of enzyme which has hydrolysis activity of glycerol phospholipids and triglycerides to the flour during bread baking process would obtain effects as described above. Moreover, pigments such as lutein and carotene in flour would affect the whiteness of flour products. If an enzyme which has hydrolysis activity of triglycerides is added to the flour to degrade fat, the fat-soluble pigments would be released and then fade more easily through oxidization. As a result, the flour products would be whitened.

In previous studies, the inventors successfully screened *Rhizopus chinensis* CCTCC M 201021 from Luzhou-flavor liquor brewing koji, which has a high yield of lipase and cloned the lipase gene from the genome for the first time and then the recombinant strain achieved high level secretion for the lipase in *Pichia pastoris* (Yu Xiao-Wei et al J Mol Catal B: Enzym, 2009, 57: 304-311). The inventors also used the lipase gene as the template and obtained a series of variants with improved thermostability by directed evolution (Granted patent: CN 101974499B; Yu Xiao-Wei et al. *Microbial Cell Factories*, 2012, 11:102-112). Then, the lipase gene from *R. chinensis* was mutated by molecular biology in this invention and heat resistant variants with hydrolytic activity of triglyceride and lecithin were obtained. The variants performed better at whitening bread or other products during processing of flour products and increasing the specific volume in bread baking process. As a granted patent CN 102160562 B has disclosed, the parent lipase as an additive has improved the baking characteristics of bread baking, while the present invention provides more excellent lipase variants which could be used in processing of flour products.

DETAILED DESCRIPTION

The goal of the present invention is to provide a novel lipase variant, which has one of the characteristics described as follows:

(1) whose amino acid sequence comprises one of the substitutions relative to the parent amino acid sequence shown in SEQ ID NO.1:

mutant 1: P298T (Proline→Threonine);
mutant 2: P298T/H317P (Proline→Threonine and Histidine→Proline);
mutant 3: P298T/H317P/V326S (Proline→Threonine, Histidine→Proline and Valine→Serine);
mutant 4: P298T/T218S/S234F (Proline→Threonine, Threonine→Serine and Serine→Phenylalanine);
mutant 5: P298T/H317P/P168L/A129S (Proline→Threonine, Histidine→Proline, Proline→Leu and Alanine→Serine);
mutant 6: P298T/S234F/K161R/V326S (Proline→Threonine, Serine→Phe, Lysine→Argnine and Valine→Serine);

(2) by deletion, substitution, insertion or mutation of one or more bases, a nucleotide sequence of the lipase has at least 80% identity with a nucleotide sequence encoding the amino acid sequence described in (1), and the lipase maintains a triglyceride and lecithin hydrolysis activity and good performance in thermostability.

The lipase variant exhibits better thermostability, and its half-life is prolonged by 14-38 fold at 40° C. than the parent lipase.

The present invention also provides a genetic engineering strain harboring a sequence encoding the lipase variant and its construction. DNA sequence encoding the lipase variants and genetically engineered bacteria or transgenic cell lines harboring the DNA sequence is also in the true scope of the present invention.

The genetic engineering strain is *P. pastoris* GS115, KM71 or SMD1168, and preferred GS115.

The present invention also provides a method of constructing the genetic engineering strain. Expression vector pPIC9, pPIC3K, pPIC9K, pAO815 or pPICZα is selected to construct a recombinant expression vector and *P. pastoris* GS115 is selected as the host to express the lipase variant. More preferably, the expression vector is pPIC9.

Application of the above lipase variants in processing of flour products also belongs to the true scope of the present invention. The flour products comprise bread, steamed bread and noodles.

Nomenclature for amino acid modifications in the present invention is explained in detail as follows.

The mutated amino acid in the variant is marked as "original amino acid, position, substituted amino acids". For example, S234F indicates a substitution of Ser in position 234 with Phe. The position number corresponds to the amino acid sequence of the parent lipase shown in SEQ ID NO: 1, and L180H/T128S indicates the position of 180 and 218 are both mutated.

The lipase variants provided in the present invention are thermostable and have triglyceride hydrolysis activity and lecithin hydrolysis activity. While they can significantly whiten the bread or other products and significantly increase the specific volume in bread baking process, the lipase variants have good application in processing of flour products.

Embodiments

Media:
LB liquid medium: 10 g·L$^{-1}$ trypton, 5 g·L$^{-1}$ yeast extract, 10 g·L$^{-1}$ NaCl, pH7.0.
MD (Minimal dextrose medium): 13.4 g L$^{-1}$ YNB, 4×10$^{-4}$ g L$^{-1}$ biotin, 20 g·L$^{-1}$ dextrose, 20 g·L$^{-1}$ agar.

BMGY (Buffered glycerol-complex medium): 10 g·L$^{-1}$ yeast extract, 20 g·L$^{-1}$ trypton, 13.4 g L$^{-1}$ YNB, 4×10$^{-4}$ g L$^{-1}$ biotin, 10 g·L$^{-1}$ glycerol, pH 6.0 100 mM potassium phosphate.

BMMY (Buffered methanol-complex medium): 10 g·L$^{-1}$ yeast extract, 20 g·L$^{-1}$ trypton, 13.4 g L$^{-1}$ YNB, 4×10$^{-4}$ g L$^{-1}$ biotin, 5 g·L$^{-1}$ methanol, 100 mM potassium phosphate.

EXAMPLE 1

Construction of Recombinant Expression Vector by Site-directed Mutagenesis

The pre-constructed plasmid pPIC9K-proRCL (Wang Lele et al. Cloning and expression of pro- and mature *Rhizopus chinensis* lipase in *Pichia pastoris*. The high-tech communications, (2009), 19 (10): 105) contains the lipase gene of the parent strain *R. chinensis* CCTCC M201021 and it was used as a template. Site directed mutagenesis kit (QuikChange II XL Site-Directed Mutagenesis Kit, Agilent) was used to obtain the following six mutated plasmids:
mutant 1: P298T;
mutant 2: P298T/H317P,
mutant 3: P298T/H317P/V326S,
mutant 4: P298T/T218S/S234F,
mutant 5: P298T/H317P/P168L/A129S,
mutant 6: P298T/S234F/K161R/V326S.

EXAMPLE 2

Construction of Recombinant Strain Expressing the Lipase Variant

The mutated plasmid was transformed into competent cells by heat shock. The positive strains were then selected from the LB media containing ampicillin. And then the plasmids were extracted from the strains and sequenced for verification.

The extracted correct mutated plasmid was digested with restriction endonuclease Sal I and then collected and condensed. Then, the linearised plasmid was mixed with 80 μL competent *P. pastoris* GS115 and removed to 0.2 cm cuvette for electric shock. The shock was conducted at voltage of 1500 V with the capacitance of 25 μF and the resistance of 200Ω.

After the shock, 1 mL pre-icecold sorbitol solution with a concentration of 1 mol/L was immediately added and mixed. Then the mixture was standing at 30° C. for 1h before applying on MD plate to screening the corrected recombinant which integrated the target gene to its chromosome. The yeast genome was extracted and amplified by primers 5'AOX and 3'AOX for PCR identification. As a negative control, the strain contained the empty vector was used to validate that the target gene had been integrated into the yeast genome.

EXAMPLE 3

Expression and Secretion of the Lipase Variant and its Separation and Purification The positive recombinant yeast was cultivated in 25-50 mL of BMGY medium in 250 mL glass flasks. When cultures reached an OD of 2.0-6.0, the cells were centrifuged and resuspended with 25-50 mL of BMMY medium shaken at 20-30° C. and 100-250 rpm for 72-144 h. Methanol was added with an amount of 1% of the broth volume every 24 h.

Protein separation and purification was achieved by the following steps.

(1) Concentrated by 10 KD Ultrafiltration 100 mL broth was centrifuged at 4° C. and 4000 rpm for 20 min. Then the supernatant was filtered by 0.22 μm microporous membrane and concentrated to about 10 mL through an 10 KD ultrafiltration. The concentrated enzyme solution was interchanged overnight with 0.02 mol/L HAc-NaAc buffer (pH 5.0) at 4° C.

(2) purified by strong cation exchange chromatography

The interchanged solution was loaded onto a pre-equilibrated SP-Sepharose FF column (1.6 cm×20 cm) and eluted with the same buffer (0.02 mol/L pH 5.0 HAc-NaAc buffer) to remove the unadsorbed protein. Then the absorbed protein was eluted with 0-0.5 M NaCl in the same buffer at a flow rate of 1 mL/min. The lipase activity component was concentrated stepwise and interchanged overnight with 0.05 M potassium phosphate buffer (pH7.5) containing 1.6 M ammonium sulfate at 4° C. for use.

(3) Purified by Hydrophobic Interaction Chromatography

The interchanged enzyme solution of step 2 was then treated with a Phenyl-sepharose 6 FF column (1.6 cm×20 cm). 0.05 M potassium phosphate buffer (pH7.5) containing 1.6 M ammonium sulfate was used as the equilibration buffer and also used to elute the unadsorbed protein. Lipase was then eluted by an ammonium sulfate concentration gradient of 0.4 M in 0.05 M potassium phosphate buffer (pH7.5) and then eluted with water at a flow rate of 0.8 mL/min. And 4 mL fractions containing the activity component were collected, interchanged and then freeze-dried for use.

EXAMPLE 4

Lipase Properties (1) Hydrolysis Activity (a) Determination of Triglyceride Hydrolysis Activity 10 mL water was added to 200 mg olive oil and 100 mg arabic gum. The mixture was then emulsified by stirring at 10000 rpm for 5 min. Next, the 200 μL emulsified solution, 100 μL 0.2 M MOPS buffer (pH 6) and 20 μl 0.1 M calcium chloride solution was mixed and held at 40 ° C. for 5min. Then 40 μL enzyme solution was added, mixed and held at 40 ° C. for 5min before 40 μL hydrochloric acid (1N) was added to terminate the enzymatic reaction. Finally, 400 μL, 4% TRITON-X-100 (CAS Number 9002-93-1, Polyethylene glycol tert-octylphenyl ether) was added to the mixture to release the free fatty acids.

(b) Determination of Lecithin Hydrolysis Activity

In this case, lecithin was used as a substrate. At first, 10 mL water was added to 200 mg lecithin and 400 μL TRITON-X-100 (Polyethylene glycol tert-octylphenyl ether). The mixture was then emulsified by stirring at 10000 rpm for 5 min. Next, the 500 μL emulsified solution, 250 μL 0.2 M MOPS buffer (pH 6) and 20 μL 0.1 M calcium chloride solution was mixed and held at 40 ° C. for 5min. And then 40 μL enzyme solution was added, mixed and held at 40 ° C. for 10min before 100 μL hydrochloric acid (1N) was added to terminate the enzymatic reaction. Finally, 400μL, 4% TRITON-X-100 (Polyethylene glycol tert-octylphenyl ether) was added to the mixture to release the free fatty acids.

The method of quantifying the free fatty acids was as follows. 3 mL free fatty acid quantitative reagent NEFA was added to 30 μL the above reaction mixture and then kept at 40° C. for 10 min.

One unit of enzyme activity was defined as the amount needed to release 1 μmol fatty acid per minute under 40° C. and pH 6.0.

The results were shown in Table 1. The ratio of the triglyceride hydrolysis activity and lecithin hydrolysis activity of the purified lipase variants were decreased from 4.9 to 1.5-3.2, indicating that the lecithin hydrolysis activity of the variants was increased compared to the triglyceride hydrolysis activity.

(2) Thermal Stability

The determination of half-life of the enzyme at 40° C. was carried out by the following steps. The enzyme solution was treated in 40° C. at various time intervals and the percentage (%) of residual triglyceride hydrolysis activity was determined. The time (min) was set as the X-axis and the logarithm of the percentage (%) of residual activity was set as the Y-axis. The inactivation constant kinact $k_{inact}$ was determined by the slope and the half-life of the enzyme ($t_{50}$) at 40° C. was determined by $t_{50}=\ln 2/k_{inact}$.

Results of thermal stability (Table 1) showed that the half-life of the variants at 40° C. were prolonged by 14-38 fold compared with the parent lipase.

TABLE 1

Enzymatic properties of lipase

| Enzyme | Ratio of triglyceride hydrolysis activity and lecithin hydrolysis activity (U/mg:U/mg) | Prolonged fold of thermal stability compared to the parent lipase |
|---|---|---|
| the parent lipase | 4.9 | — |
| mutant 1 | 3.2 | 14 |
| mutant 2 | 2.7 | 25 |
| mutant 3 | 1.8 | 18 |
| mutant 4 | 2.9 | 29 |
| mutant 5 | 2.2 | 38 |
| mutant 6 | 1.5 | 27 |

EXAMPLE 5

Application of Lipase Variants in Bread Baking

The bread baking experiments mainly focused on the impact of the lipase on the bread specific volume, and the application effect was compared between the parent lipase and the variants.

The preparation of bread was referenced to the AACC 10-10B method with a few modification. 100% flour, 1% salt, 4% sugar, 4% butter, 1.5% yeast and 62.5% water (according to the wheat mass) were mixed and lipase was added to it with an amount of 500 U/kg, while the amount of lipase in the blank control was zero. The mixture were stirred in a stirrer for 10 min, and then stood for 10 min before divided into 100 g. Next, the mixture was rounded, and stood for 10 min again. The dough was formed and put on plates and then proofed at 38° C. with a relative humidity of 85% for 90 min. Finally, the dough was baked for 25 min (upper-side temperature was 170° C. and lower-side temperature was 210° C.).

The determination of bread specific volume was carried out according to the rapeseed exclusion method. The volume and weight of the bread were measured after cooling at room temperature for 1h.

The specific volume (mL/g)=volume (mL)/weight (g).

The increased specific volume (%)=(the specific volume of sample−the specific volume of blank control)/the specific volume of blank control*100%

The results were shown in Table 2. It indicated that the maximum increased specific volume of the bread adding the lipase variant was 28%, while the parent lipase was 21%. It is clearly that the lipase variants of the present invention can significantly increase the specific volume of bread and making it a highly promising candidate for future applications in bread baking.

TABLE 2

Results of application of lipase in flour products

| Enzyme | The increased specific volume (%) | The increased whiteness compared with the blank control |
|---|---|---|
| the parent lipase | 21 | 1.3 |
| mutant 1 | 22 | 1.6 |
| mutant 2 | 27 | 1.7 |
| mutant 3 | 23 | 2.2 |
| mutant 4 | 28 | 1.8 |
| mutant 5 | 25 | 1.9 |
| mutant 6 | 24 | 2.3 |

EXAMPLE 6

Application of Lipase Variants in Steamed Bread

The experiments mainly focused on the impact of the lipase to the whiteness of the flour products such as steamed bread. And the application effect was compared between the parent lipase and the variants.

The preparation of steamed bread was carried out according to the following method. The materials were original steamed bread powder without any improver and 0.8% yeast (Angel Yeast Co., Ltd.). The added amount of lipase was 500 U/kg, while the blank control was zero. 40% water was added to the materials above and mixed thoroughly. The mixture was pressed (the dough was pressed into pieces and folded and then pressed for six times), hand-formed, proofed (proofed in the dough proofing machine at 37.5° C. with a relative humidity of 80%) and then steamed for 20 min.

The whiteness was determined by averaging the whiteness of eight random position of the steamed bread.

The increased whiteness of the blank control was set as 0. Results (shown in Table 2) indicated that the maximum increased whiteness of steamed bread adding lipase variants was 2.3 units, while it was 1.3 in the steamed bread adding parent lipase. Obviously, the lipase variants in the present invention can significantly increase the whiteness of flour products such as steamed bread, which indicating a highly promising applications in processing of flour products.

While the present invention has been described in some detail for purposes of clarity and understanding, one skilled in the art will appreciate that various changes in form and detail can be made without departing from the true scope of the invention.

What is claimed is:

1. A method of processing flour products with a lipase mutant,
   wherein the lipase mutant comprises:
   an amino acid sequence with substitutions selected from the group consisting of P298T, P298T/H317P, P298T/H317P/V326S, P298T/T218S/S234F, P298T/H317P/P168L/A129S, and P298T/S234F/K161R/V326S, wherein the substitutions are relative to a parent amino acid sequence set forth in SEQ ID NO: 1;
   wherein the lipase mutant maintains a triglyceride and lecithin hydrolysis activity and thermostability; and
   wherein the method comprises:
   expressing the lipase mutant from a culture of a recombinant yeast strain comprising an expression vector for the lipase mutant;
   preparing a purified form of the lipase mutant from the culture; and
   adding the purified form of the lipase mutant to a flour and water mix to obtain flour products.

2. The method of claim 1, wherein the flour products comprise bread, steamed bread and noodles.

* * * * *

SEQUENCE LISTING

<160> NUMBER OF SEQ ID NOS: 1

<210> SEQ ID NO 1
<211> LENGTH: 389
<212> TYPE: PRT
<213> ORGANISM: Rhizopus chinensis

<400> SEQUENCE: 1

```
Met Val Ser Phe Ile Ser Ile Ser Gln Gly Val Ser Leu Cys Leu Leu
1               5                   10                  15

Val Ser Ser Met Met Leu Gly Ser Ser Ala Val Pro Val Ala Gly His
            20                  25                  30

Lys Gly Ser Val Lys Ala Thr Asn Gly Thr Asp Phe Gln Leu Pro Pro
        35                  40                  45

Leu Ile Ser Ser Arg Cys Thr Pro Pro Ser His Pro Glu Thr Thr Gly
    50                  55                  60

Asp Pro Asp Ala Glu Ala Tyr Tyr Ile Asn Lys Ser Val Gln Trp Tyr
65                  70                  75                  80

Gln Ala His Gly Gly Asn Tyr Thr Ala Leu Ile Lys Arg Asp Thr Glu
                85                  90                  95

Thr Val Gly Gly Met Thr Leu Asp Leu Pro Glu Asn Pro Pro Pro Ile
            100                 105                 110

Pro Ala Thr Ser Thr Ala Pro Ser Ser Asp Ser Gly Glu Val Val Thr
        115                 120                 125

Ala Thr Ala Ala Gln Ile Lys Glu Leu Thr Asn Tyr Ala Gly Val Ala
130                 135                 140

Ala Thr Ala Tyr Cys Arg Ser Val Pro Gly Thr Lys Trp Asp Cys
145                 150                 155                 160

Lys Gln Cys Leu Lys Tyr Val Pro Asp Gly Lys Leu Ile Lys Thr Phe
                165                 170                 175

Thr Ser Leu Leu Thr Asp Thr Asn Gly Phe Ile Leu Arg Ser Asp Ala
            180                 185                 190

Gln Lys Thr Ile Tyr Val Thr Phe Arg Gly Thr Asn Ser Phe Arg Ser
        195                 200                 205

Ala Ile Thr Asp Met Val Phe Thr Phe Thr Asp Tyr Ser Pro Val Lys
210                 215                 220

Gly Ala Lys Val His Ala Gly Phe Leu Ser Ser Tyr Asn Gln Val Val
225                 230                 235                 240

Lys Asp Tyr Phe Pro Val Val Gln Asp Gln Leu Thr Ala Tyr Pro Asp
                245                 250                 255

Tyr Lys Val Ile Val Thr Gly His Ser Leu Gly Gly Ala Gln Ala Leu
            260                 265                 270

Leu Ala Gly Met Asp Leu Tyr Gln Arg Glu Lys Arg Leu Ser Pro Lys
        275                 280                 285

Asn Leu Ser Ile Tyr Thr Val Gly Cys Pro Arg Val Gly Asn Asn Ala
290                 295                 300

Phe Ala Tyr Tyr Val Asp Ser Thr Gly Ile Pro Phe His Arg Thr Val
305                 310                 315                 320

His Lys Arg Asp Ile Val Pro His Val Pro Pro Gln Ala Phe Gly Tyr
                325                 330                 335

Leu His Pro Gly Val Glu Ser Trp Ile Lys Glu Asp Pro Ala Asp Val
            340                 345                 350

Gln Ile Cys Thr Ser Asn Ile Glu Thr Lys Gln Cys Ser Asn Ser Ile
        355                 360                 365
```

-continued

```
Val Pro Phe Thr Ser Ile Ala Asp His Leu Thr Tyr Phe Gly Ile Asn
    370                 375                 380

Glu Gly Ser Cys Leu
385
```